US008617575B2

(12) United States Patent
Ito et al.

(10) Patent No.: US 8,617,575 B2
(45) Date of Patent: Dec. 31, 2013

(54) METHODS FOR CONFERRING IMMUNITY AGAINST PROTOZOANS IN AN ANIMAL (75) Inventors: Akira Ito, Kitamoto (JP); Toru Gotanda, Kitamoto (JP); Shigeki Kobayashi, Kitamoto (JP); Katsumi Kume, Kitamoto (JP); Takeshi Matsumura, Sapporo (JP)

(73) Assignees: Kitasato Daiichi Sankyo Vaccine Co., Ltd., Saitama (JP); National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 11/597,879

(22) PCT Filed: May 30, 2005

(86) PCT No.: PCT/JP2005/009851
§ 371 (c)(1),
(2), (4) Date: Jun. 29, 2007

(87) PCT Pub. No.: WO2005/116216
PCT Pub. Date: Dec. 8, 2005

(65) Prior Publication Data
US 2008/0003243 A1 Jan. 3, 2008

(30) Foreign Application Priority Data

May 31, 2004 (JP) ................. 2004-160666

(51) Int. Cl.
*A61K 39/00* (2006.01)
*A61K 39/002* (2006.01)
*C12N 1/20* (2006.01)
*C12N 15/00* (2006.01)
*C12N 15/82* (2006.01)
*C12N 15/30* (2006.01)
*C07K 14/00* (2006.01)
*A01H 5/00* (2006.01)

(52) U.S. Cl.
USPC ........ 424/269.1; 800/278; 800/298; 800/288; 435/468; 435/469; 424/184.1; 530/350

(58) Field of Classification Search
None
See application file for complete search history.

(56) References Cited

U.S. PATENT DOCUMENTS

2002/0006411 A1* 1/2002 Arntzen et al. ............ 424/192.1

FOREIGN PATENT DOCUMENTS

| JP | 4-501801 | 8/1992 | |
| JP | 7-284392 | 10/1995 | |
| JP | 07284392 | * 10/1995 | C12N 15/09 |
| JP | 10-507916 | 8/1998 | |
| JP | 2002-533068 | 10/2002 | |
| JP | 2003-512076 | 4/2003 | |
| WO | WO 90/02484 | 3/1990 | |
| WO | WO 95/23229 | 8/1995 | |
| WO | WO 96/12801 | 5/1996 | |
| WO | WO 96/40229 | 12/1996 | |
| WO | WO 00-37609 | 6/2000 | |
| WO | WO 01/31045 | 5/2001 | |

OTHER PUBLICATIONS

Ghosh et al. Expression of *Plasmodium falciparum* C-terminal region of merozoite surface protein (PfMSP119), a potential malaria vaccine candidate, in tobacco. (2002) Plant Science, vol. 162, pp. 335-343.*
Itoh et al. The correlation of protective effects and antibody production in immunized chickens with recombinant R7 vaccine against *Leucocytozoon caulleryi*. (2002) J. Vet. Med. Sci.; vol. 64; pp. 405-411.*
Giddings et al. (2000) "Transgenic plants as factories for biopharmaceuticals." Nat Biotechnol. 18(11): 1151-55.
Itoh, et al., "The correlation of protective effects and antibody production in immunized chickens with recombinant R7 vaccine against *Leucocytozoon caulleryi*," Journal of Veterinary Medical Science, vol. 64, No. 5, May 2002, pp. 402-411.
Ito, et al., "Field efficacy of recombinant R7 vaccine against chicken *leucocytozoonosis*," Journal of Veterinary Medical Science, vol. 66, No. 5, May 2004, pp. 483-487.
Walmsley, et al., "Plant cell factories and mucosal vaccines," Current Opinion in Biotechnology, vol. 14, No. 2, Apr. 2003, pp. 145-150.
Hansen, "Production of recombinant antigens in plants for animal and human immunization—a review," Brazilian Journal of Genetics [Online], vol. 20, No. 4, Dec. 1997, pp. 1-11.
Ito, et al., "Increase of antibody titer against *Leucocytozoon caulleryi* by oral administration of recombinant R7 antigen," Journal of Veterinary Medical Science, vol. 67, No. 2, Feb. 2005, pp. 211-213.
Isobe, et al., "Immunization of Chickens with Schizont and Serum-soluble Antigens of *Leucocytozoon caulleryi* against Leucocytozoonosis", Jpn. J. Parasitol., vol. 37, No. 4, p. 214-219, Aug. 1988.
Morii, et al., "Protective immunity to *Leucacytozoon caulleryi* Chickens by a killed vaccine", Parasitol. Res., vol. 76, p. 630-632, 1990.

(Continued)

Primary Examiner — Cathy Kingdon Worley
Assistant Examiner — Stephen Uyeno
(74) Attorney, Agent, or Firm — Hunton & Williams LLP (57) ABSTRACT Immunity against protozoan is conferred on an animal by a method comprising orally administering to an animal a transformed plant cell comprising a polynucleotide encoding a protective antigen against protozoiasis development, a transformed plant or its progeny or clone comprising the transformed cell, a propagation material of the plant or its progeny or clone, a processed material or extract of the above cell, plant, or its progeny or clone, or propagation material, or a protective antigen against protozoiasis development isolated from the transformed plant cell or the transformed plant or its progeny or clone.

14 Claims, 3 Drawing Sheets

(56) References Cited

OTHER PUBLICATIONS

Shiihara, et al., "Studies on Methods for Preventing Leukocytozoonosis (First Report),", Shizuokaken Youkei Shikenjyo Kenkyu Houkoku, vol. 13, p. 25-27, 1978.

Gotanda (2001) Journal of the Japanese Society on Poultry Disease 37(1): 2-13 [English language abstract].

Hansen (1997) "Production of Recombinant Antigens in Plants for Animal and Human Immunization—a Review." Brazilian Journal of Genetics 20(4): 1-11.

Tsuboi, et al. (2008) "Wheat Germ Cell-Free System-Based Production of Malaria Proteins for Discovery of Novel Vaccine Candidates." Infection and Immunity 76(4): 1702-1708.

Tsuboi, et al. (2010) "An efficient approach to the production of vaccines against the malaria parasite." Methods Mol Biol. 607: 73-83.

Walmsley and Arntzen (2003) "Plant cell factories and mucosal vaccines." Current Opinion in Biotechnology 14: 145-150.

Webster, et al. (Dec. 2009) "Production and characterization of an orally immunogenic *Plasmodium* antigen in plants using a virus-based expression system." Plant Biotechnol J. 7(9):846-55.

Arakawa, et al. (1998) *Experimental Medicine* (*Jikken Igaku*) 16(17): 2224-2226.

Gotanda (2001) *Journal of the Japanese Society on Poultry Diseases* 37(1): 2-13.

Matsumura (2003) Nikkei Biobusiness 55.

Nakata (2000) *Virus* 50(2): 185-195.

\* cited by examiner

S : SIZE MARKER ( λ BstP I )
C : UNTRANSFORMED POTATOES
5 : R7 GENE-INTRODUCED POTATOES (No. 5)
4 : R7 GENE-INTRODUCED POTATOES (No. 4)

FIG. 3

METHODS FOR CONFERRING IMMUNITY AGAINST PROTOZOANS IN AN ANIMAL

This application is a National Phase filing of PCT/JP2005/009851, filed May 30, 2005, which claims priority to Japanese Patent Application JP 2004-160666, filed May 31, 2004.

TECHNICAL FIELD

The present invention relates to plant-expressed oral antiprotozoiasis vaccines that use protective antigens against protozoiasis development.

BACKGROUND ART

Chicken leucocytozoonosis is a disease resulting from infection by *Leucocytozoon caulleryi* belonging to the suborder Haemosporina. *L. caulleryi* was recognized for the first time in 1909 in Vietnam in the blood of chicken as round gametocytes that do not carry malaria particles, and was named as a protozoan belonging to the genus *Leucocytozoon*.

In Japan, chicken leucocytozoonosis was confirmed for the first time in 1954 in Hyogo prefecture. The pathogen was identified as *L. caulleryi*, and thereafter, experiments demonstrated that this protozoan is biologically transmitted by a type of blood-sucking insect, *Culicoides arakawae* (hereinafter abbreviated as *C. arakawae*) belonging to the order Diptera and family Ceratopogonidae. The life cycle of this pathogen has been almost fully elucidated. *Leucocytozoon caulleryi* has three stages of development: schizogony (multiplicative reproduction) and gametogony (gamete formation) in the body of the chicken host, and sporogony (spore formation) in the body of the *C. arakawae* transmitter.

When *C. arakawae* infected with this protozoan sucks blood, sporozoites that enter the body of chicken with the saliva become parasitic on vascular endothelial cells, mainly in the lung, liver, spleen, kidney and such, and form first-generation schizonts. On the fifth to seventh day after infection, first-generation merozoites are released into the blood. These first-generation merozites reenter the vascular endothelial cells distributed throughout the body, grow into second-generation schizonts, leave the host cells and grow in the intercellular space in the late stage. On the 14th day, second-generation merozoites are released into the blood by these schizonts. The merozoites enter erythroid cells and grow, and on the 18th to 19th day, they separate from the host cells and mature as macrogametocytes (female gametocytes) and microgametocytes (male gametocytes).

When *C. arakawae* sucks blood, both gametocytes are taken up into the midgut together with the blood of the chicken. These gametocytes form macrogametes (female gametes) and microgametes (male gametes), which then conjugate (fertilization) to form zygotes that subsequently form ookinetes which enter the intercellular space in the midgut wall and develop into oocysts after migrating to beneath the outer membrane of the midgut wall. Several tens of sporozoites are formed inside the oocysts, and as the wall of the oocysts breaks down, sporozoites are released into the celom of *C. arakawae*. They then migrate to the salivary gland to complete the developmental cycle.

Symptoms and lesions in chicken caused by this protozoan infection are observed mainly in the late stages of schizogony when second-generation schizonts grow, and in the gametogony stage when second-generation merozoites become parasitic on erythroid cells and develop into gametocytes. Anemic symptoms and bleeding lesions in various organs and tissues, which are most characteristic of this disease, are thought to be triggered by vascular emboli-accompanying bleeding caused by second-generation schizonts, and disruption of red blood cells due to parasitization by protozoans in the gametogonic stage.

Since *C. arakawae*, the mediator of the protozoan, inhabits wetlands, this infection has been observed to be prevalent in Southeast Asia, China, North Korea, and South Korea where paddy fields are found. In Japan, since the first observation of leucocytozoonosis, the epidemic has recurred every summer and inflicted a significant loss on poultry productivity. However, the occurrence sharply decreased after feeds started to be supplemented with pyrimethamine (since 1964) and a mixture of pyrimethamine and sulfa drugs (since 1968) as preventive agents. Since then however, acquired resistance of protozoans and residuality issues have restricted the duration of use of effective drugs, and the use of some of these drugs have been banned for safety reasons. Such restrictions are making the prevention of the disease difficult and the damages are also becoming constant issues.

Conventional experimentally produced vaccines against chicken leucocytozoonosis include live vaccines that use sporozoites, inactivated vaccines in which the antigen is a parasite-derived substance, and inactivated vaccines produced out of organ emulsions of protozoan-infected chicken. In the case of live vaccines using sporozoites, chickens are immunized with a small number of sporozoites separated from the salivary glands of *C. arakawae* [see Non-Patent Document 1]. Examples of inactivated vaccines in which the antigen is a parasite-derived substance are as follows.

Examples of parasite-derived antigens include first-generation schizonts, first-generation merozoites, second-generation schizonts, second-generation merozoites, and soluble antigens derived from the body of chicken and from developing chick embryos. Of these, soluble antigens detected in the serum of infected chicken on the tenth to fifteenth day after sporozoite inoculation have been observed to have nearly the same antigenic characteristics as second-generation schizonts, and a relatively strong immunogenicity similar to that of the second-generation schizonts. Utility has been confirmed for experimental vaccines produced by inactivating such serum-derived antigenic material with formalin [see Non-Patent Document 2].

Furthermore, inactivated vaccines made from organ emulsions were developed to improve the difficulties of obtaining large amounts of the above-described protozoan antigens. The vaccines were experimentally produced out of organ emulsions collected from the thymus, lung, liver, spleen, kidney, and F sac from infected chicken on the thirteenth day after sporozoite inoculation, and then inactivated with formalin. The effects of such vaccines have been confirmed [see Non-Patent Document 3].

To enable a stable and abundant supply of vaccines, the present inventors have provided vaccines that use genetically modified microorganisms made to express immunogenic proteins derived from second-generation schizonts of *Leucocytozoon caulleryi* [see Patent Document 1].

However, with vaccines developed so far, there is the premise that they will be administered by injection, and is problematic in that their use is limited due to cost and inconvenience.

[Patent Document 1] Granted/Registered Japanese Patent No.3582663

[Non-Patent Document 1] Shiihara et al., "Shizuokaken Yokei Shikenjo Kenkyu Hokoku (Bulletin of Shizuoka Poultry Experiment Station)" 13:25-27 (1978)

[Non-Patent Document 2] Isobe and Suzuki, Jpn, J. Parasitol., 37:214-219 (1988)

[Non-Patent Document 3] Morii, T. et al., J. Parasitol. Res., 76:630-632 (1990)

DISCLOSURE OF THE INVENTION

Problems To Be Solved By the Invention

The present invention was achieved in view of the above circumstances. An objective of the present invention is to provide anti-protozoiasis vaccines that are economical and can be conveniently administered. More specifically, an objective of the present invention is to provide oral anti-protozoiasis vaccines with plant-expressed protective antigens against protozoiasis development.

Means To Solve the Problems

To solve the above-mentioned issues, the present inventors developed oral anti-protozoiasis vaccines utilizing transformed plants. Specifically, the R7 immunogenic protein gene derived from second-generation schizonts of *Leucocytozoon caulleryi* (Japanese Patent Application Kokai Publication No. (JP-A) H07-284392, and Granted/Registered Japanese Patent No. 3582663), was selected as antigen gene, and a vector expressing this gene was introduced into potato tubers via *Agrobacterium* to produce regenerated potato plants from the tubers. Next, the leaves of the transformants were dried and mixed with formula feed for poultry, which was orally administered to chickens that had been vaccinated beforehand with a R7 immunogenic protein derived from second-generation schizonts of *Leucocytozoon caulleryi* obtained by expression in *E. coli*. As a result, the oral administration successfully increased antibody titer in chickens. Increase in antibody titer was particularly significant in chickens having a high antibody titer level at the start of the experiment. Similar techniques can be applied to other protective antigens against protozoans.

That is, the present invention relates to oral anti-protozoiasis vaccines that use plant-expressed protective antigens against protozoiasis development, as well as production and uses thereof. More specifically, the present invention provides:

[1] a vector comprising a gene encoding a protective antigen against protozoiasis development, wherein the gene is operably linked downstream of a promoter that can be transcribed in a plant cell;

[2] a transformed plant cell introduced with a gene encoding a protective antigen against protozoiasis development;

[3] a transformed plant comprising the transformed plant cell of [2];

[4] a transformed plant which is a progeny or clone of the transformed plant of [3];

[5] a propagation material of the transformed plant of [3] or [4];

[6] a processed material or an extract of the transformant of [3] or [4], or a propagation material of said transformant, comprising a protective antigen against protozoiasis development;

[7] a method for producing a protective antigen against protozoiasis development, comprising the step of isolating a protective antigen against protozoiasis development from the transformed plant cell of [2], the transformed plant of [3] or [4], or the propagation material of [5];

[8] a method for conferring immunity against a protozoan on an animal, comprising the step of orally administering, to said animal, the transformed plant cell of [2], the transformed plant of [3] or [4], the propagation material of [5], the processed material or extract of [6], or a protective antigen against protozoiasis development obtained by the method of [7];

[9] an oral anti-protozoiasis vaccine, comprising the transformed plant cell of [2], the transformed plant of [3] or [4], the propagation material of [5], the processed material or extract of [6], or a protective antigen against protozoiasis development obtained by the method of [7]; and

[10] use of the transformed plant cell of [2], the transformed plant of [3] or [4], the propagation material of [5], the processed material or extract of [6], or a protective antigen against protozoiasis development obtained by the method of [7], in producing oral anti-protozoiasis vaccines.

BEST MODE FOR CARRYING OUT THE INVENTION

The present invention provides transformed plant cells introduced with genes encoding protective antigens against protozoiasis development.

Protozoiasis is disease that develops when protozoans, which are unicellular eukaryotes, become parasitic on living bodies. In 1975, WHO named the six major tropical diseases malaria, trypanosomiasis, leishmaniasis, filariasis, schistosomiasis, and leprosy as diseases for which preventive measures are urgently needed. Three of these are protozoan diseases and many protozoan diseases are rampant among both humans and animals.

Among them, infectious diseases caused by protozoans belonging to *Coccidiasina Haemospororina* include leucocytozoonosis caused by *Leucocytozoon caulleryi* infection and malaria (falciparum malaria, tertian malaria, quartan malaria, and ovale malaria) caused by *Plasmodium* protozoan infection. Infectious diseases caused by Haemoprotozoans belonging to *Sarcomastigophora* include leishmaniasis and trypanosomiasis, and infectious diseases caused by Haemoprotozoans a belonging to *Piroplasmia* include babesiosis and theileriosis.

"Protective antigens against protozoiasis development" are antigens that protect against the development of such protozoiases. Examples include the R7 antigen derived from second-generation schizonts of *Leucocytozoon caulleryi* (see amino acid sequence/SEQ ID NO: 1, and nucleotide sequence/SEQ ID NO: 2) against leucocytozoonosis, and AMA-1 (apical membrane antigen 1) antigen (see Cheng, Q. and Saul, T., Mol. Biochem. Parasitol., 65:183-187 (1994)), CSP (circum sporozoite protein) antigen (see Haeseleer, F. et al., Mol. Biochem. Parasitol., 57:117-126 (1993)), LSA-1 (liver stage specific antigen-1) antigen (see Yang, C. et al., Mol. Biochem. Parasitol., 71:291-294 (1995)), MSP-1 (merozoite surface protein-1) antigen (see Ranford-Cartwright, L C. et al., Mol. Biochem. Parasitol., 46:185-187 (1991)), PfEMP1 (Plasmodium falciparum infected erythrocyte membrane protein 1) antigen (see Ward, C P. et al., Mol. Biochem. Parasitol., 102:167-177 (1999)), SERA (serine repeat antigen) antigen (see Li, W B. et al., Mol. Biochem. Parasitol., 33:13-25(1989)), and TRAP (thrombospondin related adhesion protein) antigen (see Trottein, F. et al., Mol. Biochem. Parasitol., 74:129-141 (1995)) against malaria, but the protective antigens of the present invention against protozoiasis development are not limited thereto. Mutant protective antigens with modified genetic sequences or amino acid sequences are also included in such protective antigens. Naturally or artificially produced mutant protective antigens are also included.

Plants derived from the transformed plant cells of the present invention are not particularly limited so long as they are suitable for oral administration, and examples include potato, tomato, beans such as soybean and adzuki (or "azuki"), grains such as rice, wheat and corn, fruits such as strawberry, and pasture grass.

The transformed plant cells of the present invention can be produced by introducing a vector carrying a gene encoding the protective antigen against protozoiasis development into plant cells, and expressing this gene. Vectors used for gene expression in plant cells are not particularly limited so long as they include a promoter that can be transcribed in plant cells and a terminator sequence comprising a polyadenylation site necessary for stabilization of the transcription product, and examples include the "pBI121", "pBI221", and "pBI101" plasmids (all from Clontech). For example, as promoters that can be transcribed in plant cells, promoters for carrying out constitutive gene expression in plant cells, or promoters that are inductively activated by extrinsic stimuli may be used. Examples of promoters for constitutive expression include the 35S promoter of cauliflower mosaic virus (Odell et al. 1985 Nature 313:810), actin promoter of rice (Zhang et al. 1991 Plant Cell 3:1155), and ubiquitin promoter of corn (Cornejo et al. 1993 Plant Mol. Biol. 23:567). The protective antigen against protozoiasis development can be expressed inside plant cells by introducing into plant cells, vectors carrying a gene encoding the protective antigen against protozoiasis development that is operably linked to such promoters. Herein, the phrase "operably linked" means that a promoter and a gene encoding a protective antigen against protozoiasis development are linked such that the protective antigen against protozoiasis development is expressed in the plant cells. The present invention also provides vectors for producing transformed plant cells carrying such a protective antigen against protozoiasis development.

"Plant cells" that are transformed include plant cells having various morphologies such as suspension culture cells, protoplasts, leaf sections, and calli.

Vectors can be introduced into plant cells using various methods known to those skilled in the art, such as an *Agrobacterium*-mediated method, the polyethylene glycol method, electroporation method, and particle gun method.

A plant can be regenerated from a transformed plant cell by regeneration. Regeneration methods differ according to the type of plant cell, but a number of techniques have already been established and widely used in the technical field of the present invention. Such methods include, for example, for potato, the method of Visser et al. (Theor. Appl. Genet 78:594 (1989)) or the tuber disc method for plant regeneration, for monocotyledonous cereals such as rice, the method of Hiei et al. (Hiei, Y., Komari, T., Kubo, T: Transformation of rice mediated by *Agrobacterium tumefaciens*. Plant Mol Biol 1997 35:1-2 205-18), the method of Ishida et al. (Ishida, Y., Saito, H., Ohta, S., Hiei Y, Komari, T., Kumashiro, T: High efficiency transformation of maize (*Zea mays* L.) mediated by *Agrobacterium tumefaciens*. Nat Biotechnol 1996 June 14:6 745-50), electroporation method (Shimamoto, K., Terada, R., Izawa, T. et al.: Fertile transgenic rice plants regenerated from transformed protoplasts. Nature 338, 274-276 (1989)), and for strawberry, the method of Asao et al. (Asao, H., Y Nishizawa, S. Arai, T. Sato, M. Hirai, K.

Yoshida, A. Shinmyo and T. Hibi.: Enhanced resistance against a fungal pathogen *Sphaerotheca humuli* in transgenic strawberry expressing a rice chitinase gene. Plant Biotechnology. 14 (3):145-149 (1997)). In the present invention, these methods can be preferably used.

Once a transformed plant that has a gene encoding a protective antigen against protozoiasis development introduced into its genome (chromosome) is obtained, progenies can be obtained by sexual or asexual reproduction from that plant. In addition, it is possible to obtain propagation material (for example, seeds, fruits, grafts, tubers, tubercles, stubbles, calli, and protoplasts) from the plant, or from progenies or clones thereof, then use them as a source to mass-produce plants. The present invention includes plants comprising the transformed plant cells of the present invention, and progenies and clones thereof, as well as propagation materials of the plants, and their progenies and clones.

Transformed plant cells, transformed plants, or propagation materials thereof produced as described above may be used directly as vaccines for oral administration, but it is also possible to use their processed materials or extracts comprising the protective antigen against protozoiasis development. Herein, the term "processed materials" means substances produced by processing transformed plant cells, transformed plants, or propagation materials thereof into a form suitable for vaccination. In the case of transgenic potato, an example is a material produced by freeze-drying potato leaves. The term "extract" means matter obtained by extracting components comprising a protective antigen against protozoiasis development from transformed plant cells, transformed plants, or propagation materials thereof, and includes those that are purified or crudely purified. Isolation (purification) of protective antigens against protozoiasis development from transformed plant cells, transformed plants, or propagation materials thereof can be carried out using conventional protein purification methods such as salt precipitation, ultrafiltration, ion exchange chromatography and gel chromatography.

The present invention also provides methods for producing protective antigens against protozoiasis development, wherein the methods comprise such steps for isolating the protective antigens against protozoiasis development.

The present invention also provides methods for conferring immunity against protozoans on animals, wherein the methods comprise the step of orally administering the above-mentioned transformed plant cells, transformed plants, propagation materials, processed materials or extracts thereof, or protective antigens against protozoiasis development that were isolated by the above-mentioned method to the animals.

In the present invention, the animals that are the object of administration of protective antigens against protozoiasis development are, for example, birds if the protozoiasis is leucocytozoonosis, and humans, monkeys, and birds if it is malaria. Further examples include humans and dogs for leishmaniasis, humans, cattle, and horses for trypanosomiasis, dogs, cats, cattle, and horses for babesiosis, and cattle for theileriosis.

When orally administering a plant-body of the present invention carrying a protective antigen gene against protozoiasis development, the above-mentioned transformed plant cells, transformed plants, propagation materials, processed material or extracts thereof, or the isolated protective antigens against protozoiasis development may be administered alone or after mixing with other components. Examples of the other components that may be used in combination include mucosal immune adjuvants (for example, cholera toxin and cytokines), feeds of animals that are the object of administration, and additives (such as lactose) for improving palatability.

The dose differs depending on the animal that is the object of administration. For example, for chicken, mixing a plant carrying a protective antigen gene against protozoiasis development with regular feed, and feeding 2 to 5 g of this mixture per day, is thought to be convenient. For other animals, an amount converted according to body weight, or an amount converted according to body surface area may be administered, without limitation. Preferable doses can be determined by taking into account the expression level of the preventive antigen, optimum antibody production, properties of the formula feed, and such.

Oral vaccines of the present invention can also be administered to animals whose antibody titer has already been increased by vaccination (for example, vaccination by injection). This can further increase the antibody titer of such animals. For example, a significant increase of antibody titer was confirmed in the present Examples when the vaccines were orally administered to animals who had been inoculated with antigens expressed in E. coli and had high antibody titer level (animals with an ELISA absorbance value of 0.4 or more, or preferably 0.7 or more, in 3200-fold diluted serum).

All prior art references cited herein are incorporated by reference into this description.

EXAMPLES

Hereinbelow, the present invention will be more specifically described with reference to Examples, but it is not limited thereto.

Example 1

Insertion of An R7 Gene Encoding An Immunogenic Protein Derived From Second-generation Schizonts of *Leucocytozoon Caulleryi* Into A Plant Expression Plasmid The pBI-R7 expression vector of the present invention was obtained by digesting the pTH-R7 plasmid vector comprising an R7 immunogenic protein gene derived from second-generation schizonts of *Leucocytozoon caulleryi* (JP-A H07-284392, and Granted/Registered Japanese Patent No. 3582663) using SmaI and SacI restriction enzymes, and cloning the obtained R7 gene DNA fragments (SEQ ID NOs: 1 and 2) into the pBI121 plasmid vector (Clontech) carrying a cauliflower mosaic virus 35S promoter, β-glucuronidase gene, and nopaline synthase terminator, at the site digested using SmaI and SacI restriction enzymes.

Example 2

Introduction of the R7 Gene Derived From Second-generation Schizonts of *Leucocytozoon Caulleryi* Into Potato And Expression of the Gene 1. Introduction of the R7 Gene Derived From Second-generation Schizonts of *Leucocytozoon caulleryi* Into *Agrobacterium*

The pBI-R7 plasmid for expressing the R7 gene derived from second-generation schizonts of *Leucocytozoon caulleryi*, obtained as described above in Example 1, was introduced into *Agrobacterium tumefaciens* LBA 4404 (Clontech) by the direct introduction method using freeze-thaw treatment.

More specifically, *Agrobacterium tumefaciens* LBA 4404 was shake-cultured in 50 mL of LB liquid medium (1% Bactotryptone, 0.5% yeast extracts, 1% sodium chloride) at 28° C. until the absorbance at A600 reached approximately 1.0. After cooling on ice, the culture was centrifuged at 3000 g at 4° C. (using Kubota RA-4), and bacterial cells were collected and suspended in 1 mL of ice-cooled 20 mM calcium chloride solution. A 0.1-mL aliquot of this suspension was placed in each EPPENDORF tube.

One μg of the pBI-R7 recombinant plasmid was added and this was quickly frozen in liquid nitrogen. Next, the obtained frozen cells were thawed at 37° C. and then left to stand for 5 minutes. One mL of LB medium was added to these cells, and the mixture was shake-cultured at 28° C. for 2-4 hours. After centrifugation at approximately 10,000 g for 1 minute (using Kubota KM-15200) to collect the bacterial cells, the cells were suspended in 0.1 mL of LB medium, then spread onto a LB solid medium containing rifampicin (100 μg/mL), kanamycin (25 μg/mL), and streptomycin (300 μg/mL), and then cultured at 28° C. for 2-3 days to obtain transformed bacteria carrying pBI-R7.

The transformed *Agrobacterium tumefaciens* LBA4404 obtained above was shake-cultured in LB liquid medium at 28° C. and then centrifuged at 3000 g at 4° C. (using Kubota RA-6). The bacteria were then collected, suspended in MS medium [Physiol. Plant. 15:473 (1962)] and this was used for transformation of plants.

2. Introduction Into Potato By the *Agrobacterium* Method

The R7 gene derived from second-generation schizonts of *Leucocytozoon caulleryi* was introduced into potato by the tuber disc method using the Agrobacteria produced above.

More specifically, the skin of potato tubers were peeled, sterilized in 1% sodium hypochlorite solution for 15 minutes, and washed six times with sterile distilled water. A sterilized cork borer was used to excise a 1-cm diameter cylindrical section from this tuber, and the section was sliced into 2-3-mm thick disks. These discs were soaked for 15 minutes in a MS liquid medium suspension of the *Agrobacterium tumefaciens* LBA4404 carrying pBI-R7 produced in section 1 above. They were then incubated on MS medium [containing 3% sucrose, 0.1 μg/mL indole acetic acid, 0.1 μg/mL gibberellin, 0.1 μg/mL abscisic acid, and 2 μg/mL zeatin riboside (pH5.9)] at 28° C. for 3 days, and the discs were washed with MS liquid medium containing antibiotics (100 μg/mL of kanamycin and 500 μg/mL of carbenicillin (both from Sigma)).

The washed discs were subcultured onto MS solid medium containing the above-mentioned antibiotics (and also containing 3% sucrose) at 25° C. every two weeks (a 16-hour light period, and an 8-hour dark period). On the fourth to eighth week of culture, calli formed on the surface of the discs, and further subcultures induced shoots.

These shoots were cut from the base, transplanted onto MS solid medium (containing 3% sucrose, 100 μg/mL of kanamycin, and 500 μg/mL of carbenicillin (pH5.9)) that does not contain hormones, and were cultured. Plants that took root 2 to 4 weeks later were transplanted to a 10-cm diameter pot containing potting compost, and were grown inside an artificial climate chamber.

3. Confirmation of Introduction of R7 Gene Derived From Second-generation Schizonts of *Leucocytozoon Caulleryi* Into Regenerated Plants And Verification of Gene Expression (1) Confirmation of Expression of the R7 Gene Derived From Second-generation Schizonts of *Leucocytozoon Caulleryi* By ELISA Regenerated potato leaves were ground in three times the wet volume of PBS-T buffer (135 mM sodium chloride, 1.5 mM sodium dihydrogen phosphate, 2.7 mM disodium hydrogen phosphate, 0.05% (v/v) TWEEN20, pH 7.2), and the supernatant obtained by centrifugation at 3000 g for 15 minutes (using Kubota KS-5000) was used as crude sap.

Anti-*Leucocytozoon caulleryi* second-generation schizont monoclonal antibodies (Gotanda, T. et al., J. Vet. Med. Sci. 64 (3):281-283 (2002)) diluted to a concentration of 2 µg/mL in 0.05 M sodium carbonate buffer [1.59 g of disodium carbonate and 2.93 g of sodium hydrogen carbonate in one liter (pH9.6)] were dispensed into each well of 96-well ELISA plates (IWAKI), and the plates were left to stand overnight at 4° C. for coating.

The coated plates were washed with PBS-T buffer, then a blocking solution prepared by adding bovine serum albumin to PBS-T buffer to a final concentration of 3% (w/v) was dispensed into each well of the plates, and the plates were left to stand for one hour at 37° C. for blocking.

Figure 1:
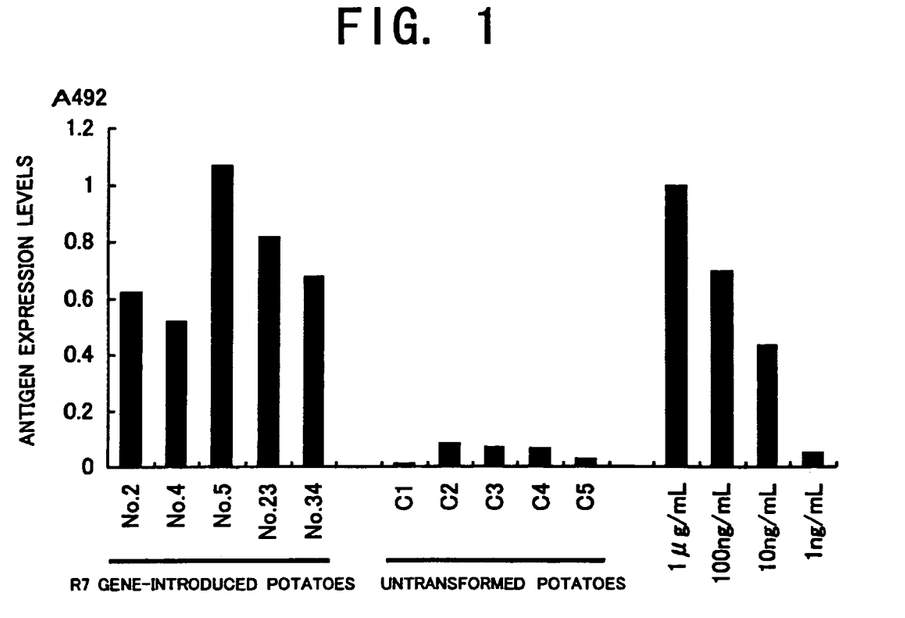
FIG. 1 shows the result of an ELISA on non-transgenic potatoes and transgenic potatoes introduced with an R7 gene derived from second-generation schizonts of *Leucocytozoon caulleryi*.

After the blocking treatment, the plates were washed with PBS-T buffer, and the crude sap of the leaves was added to the plates. The plates were then left to stand for one hour at 37° C. to allow the reaction with the antibodies to take place. After washing these plates with PBS-T buffer, HRPO-labeled anti-*Leucocytozoon caulleryi* second-generation schizont monoclonal antibodies [Ito, A. et al., J. Vet. Med. Sci. 64 (5):405-411 (2002)] diluted 4000 times in an antibody dilution prepared by adding bovine serum albumin to PBS-T buffer to a final concentration of 0.3% (w/v) were dispensed to each well of the plates, and were allowed to react for one hour at 37° C. After washing the plates with PBS-T buffer, a substrate solution (containing 14.6 g of disodium hydrogen phosphate, 10.2 g of citric acid monohydrate, 1 g of o-phenylenediamine, and 1 mL of hydrogen peroxide solution in one liter) was added to the plates and allowed to react by leaving in the dark for 15 minutes at 37° C. The reaction was stopped using a stop solution (5 N aqueous sulfuric acid solution), and absorbance at A492 was measured on a microplate reader (using Corona MTP-120). As a result, the R7 protein derived from second-generation schizonts of *Leucocytozoon caulleryi* was found to be expressed in several regenerated potato plants (see FIG. 1).

Figure 2:
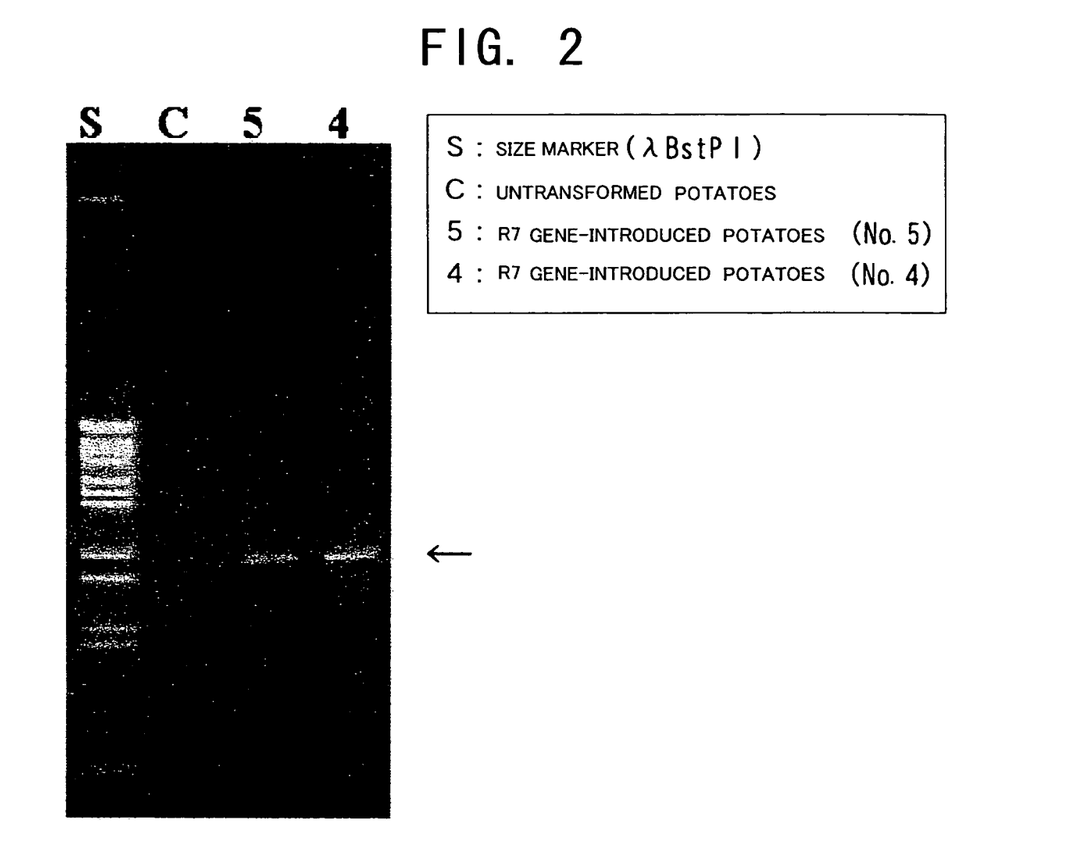
FIG. 2 is a photograph of electrophoresis showing the result of a genomic PCR performed on transgenic potatoes introduced with the R7 gene derived from second-generation schizonts of *Leucocytozoon caulleryi*.

(2) Confirmation of Introduction of the R7 Gene Derived From Second-generation Schizonts of *Leucocytozoon Caulleryi* Into Potatoes Leaves of several potato plants in which reactions were confirmed by ELISA were ground into a powder in the presence of liquid nitrogen using a mortar. RED Extract-N-Amp Plant PCR Kit (SIGMA) reagent was used according to the manufacturer's protocol to extract the total DNA of the aforementioned potato leaves, and to perform genomic PCR using the R7f primer (5'-GGAAATGTGTCCTTAACTTC-3': SEQ ID NO: 3) and R7r primer (5'-CTTCTTCTTCAT-TACTTTTC-3': SEQ ID NO: 4) that specifically amplify the R7 gene. When a portion of the reacted sample was subjected to 1.2% agarose gel electrophoresis, a band was observed at the same position as that of the R7 gene, which confirmed that the R7 gene derived from second-generation schizonts of *Leucocytozoon caulleryi* has been introduced into the chromosome in these potato plants (see the electrophoresis photograph in FIG. 2: the arrow indicates the position of the band for the R7 gene derived from second-generation schizonts of *Leucocytozoon caulleryi*).

Example 3

Confirmation of the Antigenicity of Potatoes Introduced With the R7 Gene Derived From Second-generation Schizonts of *Leucocytozoon Caulleryi*

The leaves of potatoes introduced with the R7 gene derived from second-generation schizonts of *Leucocytozoon caulleryi* were freeze-dried (a 48-hour procedure using Kyowa Shinku Gijyutsu (Kyowa Vacuum Technology) RLE-204) until the dry weight became approximately one-twelfth that of the wet weight. The dried leaves were ground into a powder, then mixed with formula feed for poultry (Funabashi Farm), and used as an oral administration.

SPF chickens (Nisseiken Co. Ltd.) subjected to oral administration tests were three hens to which the leucocytozoonosis vaccine had been injected 17 weeks earlier. The leucocytozoonosis vaccine is currently widely used in the field, and uses an R7 protein derived from second-generation schizonts of *Leucocytozoon caulleryi* expressed in *E. coli*, as the antigenic component of the vaccine (JP-A H07-284392)). A total of 60 g of the oral administration (4 g of the total was the freeze-dried leaves of potato introduced with the R7 gene) was fed per day to each chicken, and the oral administration was continued for five consecutive days (the chicken were allowed to feed freely). After the period of feeding the feed containing leaves of potato introduced with the R7 gene, 60 g of formula feed for poultry (Funabashi Farm) was fed per day to each chicken. One chicken that was used as the control was given only 60 g of the ordinary formula feed for poultry per day from the beginning of the experiment. The blood of all test chickens, including the control chicken, was collected as needed from the wing vein starting from the time when the oral administration (feeding) commenced, and the sera were obtained by centrifugation. Using these sera, antibody tests were carried out by the ELISA method described below.

Ultrasonicated and solubilized antigens from second-generation schizonts of *Leucocytozoon caulleryi* [Ito, A. et al., J. Vet. Med. Sci. 64 (5):405-411 (2002)], which were diluted to a concentration of 0.1 µg/mL in 0.05 M sodium carbonate buffer [1.59 g of disodium carbonate and 2.93 g of sodium hydrogen carbonate in one liter (pH9.6)], were dispensed into each well of 96-well ELISA plates (IWAKI), and the plates were left to stand overnight at 4° C. for coating.

The coated plates were washed with PBS-T buffer, then a blocking solution prepared by adding bovine serum albumin to PBS-T buffer to a final concentration of 3% (w/v) was dispensed into each well of the plates, and blocking performed by leaving the plates to stand for one hour at 37° C.

After the blocking treatment, the plates were washed with PBS-T buffer, and sera subjected to a two-fold stepwise dilution from 100-fold to 51,200-fold using an antibody dilution prepared by adding bovine serum albumin to PBS-T buffer to a final concentration of 0.3% (w/v) were dispensed into each well of the plates. The plates were then left to stand for one hour at 37° C. to allow the reaction with the antibodies to take place. After washing these plates with a PBS-T buffer, HRPO-labeled anti-chicken IgG (available from ZYMED) diluted 12,000 times with the antibody dilution was dispensed into each well of the plates, and was allowed to react for one hour at 37° C. After washing the plates with PBS-T buffer, a substrate solution (containing 14.6 g of disodium hydrogen phosphate, 10.2 g of citric acid monohydrate, 1 g of o-phenylenediamine, and 1 mL of aqueous hydrogen peroxide solution in one liter) was added to the plates and allowed to react by leaving the plates to stand in the dark for 15 minutes at 37° C. After stopping the reaction using a stop solution (5 N aqueous sulfuric acid solution), the absorbance at A492 was measured on a microplate reader (Corona MTP-120).

Figure 3:
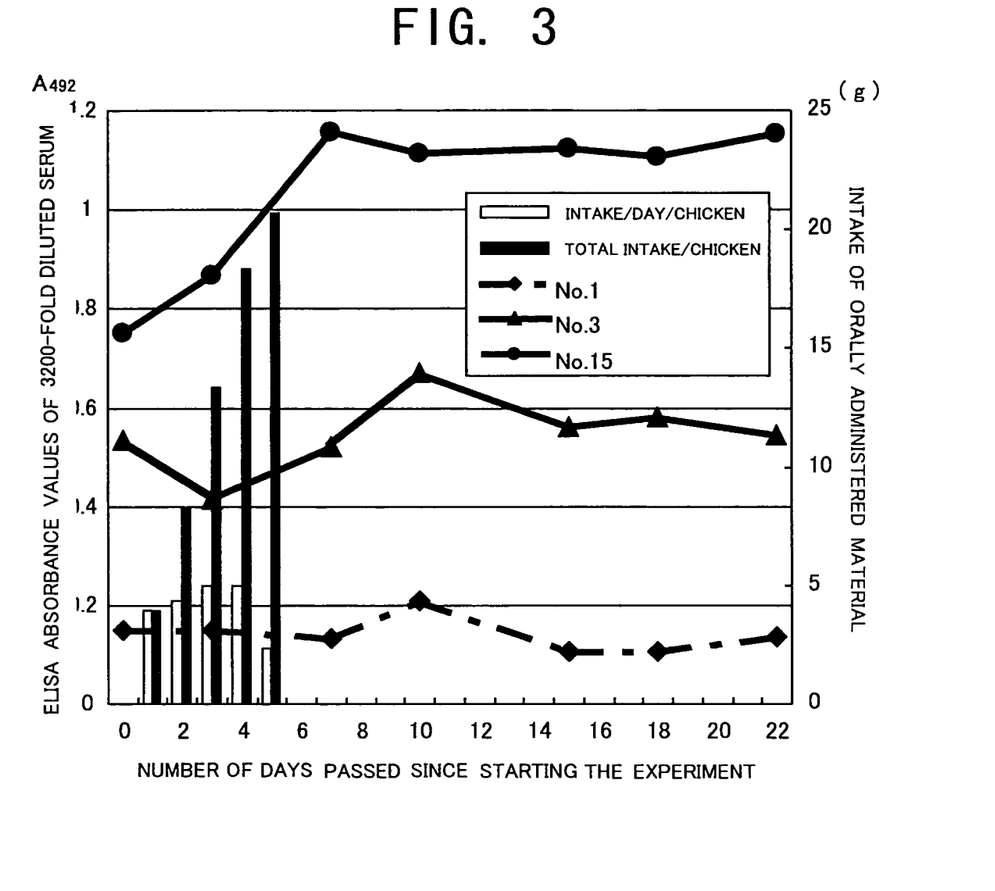
FIG. 3 shows the reinduction of blood antibodies in chickens that have been immunized by injection beforehand and have orally ingested transgenic potatoes introduced with the R7 gene derived from second-generation schizonts of *Leucocytozoon caulleryi*.

The results of this experiment are shown in FIG. 3. As seen from FIG. 3, after oral administration of the R7 gene-introduced potato leaves, antibodies against second-generation schizonts of *Leucocytozoon caulleryi* were confirmed to be re-induced in all of the tested chickens. The increase was particularly significant in chickens having a higher antibody titer level at the start of the experiment.

Industrial Application

The present invention provides (1) expression vectors for plant cells, which comprise a gene encoding a protective antigen against protozoiasis development, (2) transformed plant cells introduced with a gene encoding a protective antigen against protozoiasis development, (3) transformed plants comprising the transformed plant cells, and transformed plants that are the progenies or clones thereof, (4) propagation materials of the transformed plants, (5) processed material or extracts of the transformants or propagation materials thereof, (6) methods for producing protective antigens against protozoiasis development, comprising the step of isolating protective antigens against protozoiasis development from the transformed plant cells, the transformed plants, or the propagation materials, and (7) methods for conferring immunity against a protozoan on animals, comprising the step of orally administering an above-mentioned transformed plant cell, transformed plant, propagation material or processed material or extract thereof, or a protective antigen against protozoiasis development obtained by an above-mentioned method to these animals. The present invention has thus enabled the development of anti-protozoiasis vaccines with superior cost performance that can be conveniently administered.

The invention claimed is:

1. A method for conferring immunity against the development of leucocytozoonosis in an animal comprising orally administering to said animal:
   (a) a transformed plant cell comprising a polynucleotide encoding a protective antigen against leucocytozoonosis development, wherein said protective antigen is expressed in said plant cell and wherein said polynucleotide comprises a nucleotide sequence encoding a protein comprising the amino acid sequence of SEQ ID NO: 1 or said polynucleotide comprises the nucleotide sequence of SEQ ID NO: 2;
   (b) a transformed plant comprising said transformed plant cell;
   (c) a progeny or clone of said transformed plant, wherein said progeny or clone comprises said polynucleotide; or
   (d) propagation material of said transformed plant or progeny or clone of said transformed plant; wherein said propagation material comprises the polynucleotide encoding said protective antigen; and
   wherein said administration of said plant cell, plant, progeny, clone, or propagation material comprising said protective antigen is in a dose sufficient to result in an increased serum antibody titer of antibodies against said protective antigen.

2. The method of claim 1, wherein said transformed plant cell comprising a polynucleotide encoding a protective antigen against leucocytozoonosis development is administered to said animal.

3. The method of claim 1, wherein said transformed plant comprising said transformed plant cell is administered to said animal.

4. The method of claim 1, wherein said progeny or clone of said transformed plant is administered to said animal.

5. The method of claim 1, wherein said propagation material of said transformed plant or progeny or clone of said transformed plant is administered to said animal.

6. The method of claim 1, wherein the progeny or clone of said transformed plant, or propagation material of said transformed plant is administered to said animal.

7. The method of claim 6, wherein said propagation material is selected from the group consisting of seeds, fruits, grafts, tubers, tubercles, stubbles, calli, and protoplasts.

8. The method of claim 1, wherein said animal is a bird.

9. The method of claim 8, wherein said bird is a chicken.

10. The method of claim 1, wherein said transformed plant is freeze-dried.

11. A method for conferring immunity against the development of leucocytozoonosis in an animal comprising orally administering to said animal:
   (a) a transformed plant cell comprising a polynucleotide encoding a protective antigen against leucocytozoonosis development, wherein said protective antigen is expressed in said plant cell and wherein said polynucleotide comprises a nucleotide sequence encoding a protein comprising the amino acid sequence of SEQ ID NO: 1;

(b) a transformed plant comprising said transformed plant cell;

(c) a progeny or clone of said transformed plant, wherein said progeny or clone comprises said polynucleotide; or (d) propagation material of said transformed plant or progeny or clone of said transformed plant, wherein said propagation material comprises the polynucleotide encoding said protective antigen; and wherein said administration of said plant cell, plant, progeny, clone, or propagation material comprising said protective antigen supplies said protective antigen in a dose sufficient to result in an increased serum antibody titer of antibodies against said protective antigen.

12. A method for conferring immunity against the development of leucocytozoonosis in an animal comprising orally administering to said animal:

(a) a transformed plant cell comprising a polynucleotide encoding a protective antigen against leucocytozoonosis development, wherein said protective antigen is expressed in said plant cell and wherein said polynucleotide encoding a protective antigen against leucocytozoonosis development comprises the nucleotide sequence of SEQ ID NO: 2;

(b) a transformed plant comprising said transformed plant cell;

(c) a progeny or clone of said transformed plant, wherein said progeny or clone comprises said polynucleotide; or (d) propagation material of said transformed plant or progeny or clone of said transformed plant, wherein said propagation material comprises the polynucleotide encoding said protective antigen and wherein said administration of said plant cell, plant, progeny, clone, or propagation material comprising said protective antigen supplies said protective antigen in a dose sufficient to result in an increased serum antibody titer of antibodies against said protective antigen.

13. A method for conferring immunity against the development of leucocytozoonosis in an animal comprising orally administering to said animal a protective antigen against leucocytozoonosis development isolated from the transformed plant cell or the transformed plant or its progeny or clone, and administration of said protective antigen is in a dose sufficient to result in an increased serum antibody titer of antibodies against said protective antigen, wherein said plant cell, plant, progeny, clone, or propagation material comprising said protective antigen comprises a polynucleotide comprises a nucleotide sequence encoding a protein comprising the amino acid sequence of SEQ ID NO: 1 or said polynucleotide comprises the nucleotide sequence of SEQ ID NO: 2.

14. A method for conferring immunity against the development of leucocytozoonosis in an animal comprising orally administering to said animal:

(a) a transformed plant cell comprising a polynucleotide encoding a protective antigen against leucocytozoonosis development, wherein said protective antigen is expressed in said plant cell and wherein said polynucleotide comprises a nucleotide sequence encoding a protein comprising the amino acid sequence of SEQ ID NO: 1 or said polynucleotide comprises the nucleotide sequence of SEQ ID NO: 2;

(b) a transformed plant comprising said transformed plant cell;

(c) a progeny or clone of said transformed plant, wherein progeny or clone comprises said polynucleotide; or (d) propagation material of said transformed plant or progeny or clone of said transformed plant; wherein said propagation material comprises the polynucleotide encoding said protective antigen;

wherein said administration of said plant cell, plant, progeny, clone, or propagation material comprising said protective antigen is in a dose sufficient to result in an increased serum antibody titer of antibodies against said protective antigen and wherein said plant is an edible plant.

* * * * *

SEQUENCE LISTING

<160> NUMBER OF SEQ ID NOS: 4

<210> SEQ ID NO 1
<211> LENGTH: 774
<212> TYPE: PRT
<213> ORGANISM: Leucocytozoon caulleryi

<400> SEQUENCE: 1

```
Met Ser Thr Arg Asn Thr Tyr Pro Phe Tyr Thr Ile Gly Asn Val Ser
1               5                   10                  15

Leu Thr Ser Gly Leu Val Thr Phe Ile Ser Pro Asn Asn Val Gln Ala
            20                  25                  30

Glu Ile Ile Asn Thr His Gly Val Arg Cys Asn Gln Asn Glu Glu Val
        35                  40                  45

Thr His Gln Thr His Gln Thr His Gln Thr His Gln Thr His Gln Thr
    50                  55                  60

His Gln Thr His Gln Ile His Gln Ile His Gln Ile His Gly Tyr Met
65                  70                  75                  80

Thr Asn Gln Lys His Glu Glu His Gly Lys Ile Ile Asn Gln Val Lys
                85                  90                  95

Glu Asn Val Lys Asn Thr Val Asn Glu Asn Val Lys Asn Asn Val Asp
            100                 105                 110

Glu Asn Thr Thr Ser Glu His Glu Ile Thr Ile Pro Asn Glu Asn Asp
        115                 120                 125

Ile Lys Thr Asn Asp Glu Asn Glu Thr Thr His Tyr Glu Arg Glu Ile
    130                 135                 140

Ile Tyr Ile Val Asp Asp Leu Pro Glu Val Asn Val Glu Glu Ser Asp
145                 150                 155                 160

Glu Thr Glu His Ile Thr Tyr Glu Ile Asp Asn Asp Ile Gln Glu Glu
                165                 170                 175

His Glu Lys Val Thr His Glu Glu Glu Lys Glu Glu Val Thr His Glu
            180                 185                 190

Glu Ile Glu Lys Glu Glu His Glu Glu Val Ile His Glu Glu Glu Lys
        195                 200                 205

Glu Glu Val Thr His Glu Glu Ile Glu Lys Glu Glu His Glu Glu Val
    210                 215                 220

Ile His Glu Glu Glu Lys Glu Glu Val Thr His Glu Glu Ile Glu Lys
```

-continued

```
            225                 230                 235                 240
Glu Glu His Glu Glu Val Ile His Glu Glu Lys Glu Glu Val Thr
                245                 250                 255
His Glu Glu Ile Glu Lys Glu Glu His Glu Glu Val Ile His Glu Glu
                260                 265                 270
Glu Lys Glu Glu Val Thr His Glu Glu Ile Glu Lys Glu Glu His Glu
                275                 280                 285
Glu Val Ile His Glu Glu Lys Glu Glu Val Thr His Glu Glu Ile
                290                 295                 300
Glu Lys Glu Glu His Glu Glu Val Ile His Glu Glu Lys Glu Glu
305                 310                 315                 320
Val Thr His Glu Glu Ile Glu Lys Glu Glu His Glu Glu Val Ile His
                325                 330                 335
Glu Glu Glu Lys Glu Glu Val Thr His Glu Glu Ile Glu Lys Glu Glu
                340                 345                 350
His Glu Glu Val Ile His Glu Glu Lys Glu Glu Val Thr His Glu
                355                 360                 365
Glu Ile Glu Lys Glu Glu His Glu Glu Val Ile His Glu Glu Lys
                370                 375                 380
Glu Glu Val Thr His Glu Glu Lys Lys Glu Glu His Glu Glu Val
385                 390                 395                 400
Ile His Glu Glu Glu Lys Glu Glu Val Thr His Glu Glu Ile Glu Lys
                405                 410                 415
Glu Glu His Glu Glu Val Ile His Glu Glu Lys Glu Glu Val Thr
                420                 425                 430
His Glu Glu Lys Glu Lys Glu Glu His Glu Glu Val Ile His Glu Glu
                435                 440                 445
Glu Lys Glu Glu Val Thr His Glu Glu Glu Glu Lys Val Thr His
                450                 455                 460
Glu Glu Glu Glu Glu Lys Val Ile His Glu Glu Lys Glu Glu Val
465                 470                 475                 480
Ile His Glu Glu Glu Lys Glu Glu Val Thr His Glu Glu Glu Lys Glu
                485                 490                 495
Glu Val Thr His Glu Glu Lys Glu Glu Val Thr His Glu Glu Glu
                500                 505                 510
Lys Glu Glu Val Thr His Glu Glu Glu Lys Glu Glu Val Thr His Glu
                515                 520                 525
Glu Glu Glu Lys Val Thr His Glu Glu Glu Lys Glu Glu Val Thr His
                530                 535                 540
Glu Glu Glu Lys Glu Glu Val Thr His Glu Glu Glu Lys Val Thr
545                 550                 555                 560
His Glu Glu Glu Glu Lys Val Thr His Glu Glu Glu Glu Lys Val Thr
                565                 570                 575
Tyr Glu Glu Glu Glu Glu Glu Glu Lys Val Thr His Glu Glu Glu
                580                 585                 590
Glu Lys Val Thr His Glu Glu Glu Lys Val Ile His Glu Glu Glu
                595                 600                 605
Glu Lys Glu Glu Asp Glu Glu Glu Glu Glu Glu Glu Glu Glu Glu
                610                 615                 620
Glu Glu Glu Glu Glu Glu Asp Glu Glu Glu Glu Glu Glu Glu Glu
625                 630                 635                 640
Asp Glu Glu Glu Glu Glu Glu Glu Glu Asn Glu Glu Glu Glu Glu
                645                 650                 655
```

```
Glu Asn Glu Glu Glu Glu Glu Glu Glu His Glu Glu Val
        660                 665                 670
Thr His Glu Glu Glu Glu Glu Lys Val Thr His Glu Glu Glu
        675                 680                 685
Lys Val Thr His Glu Glu Glu Asn Val Thr Tyr Glu Glu Glu
        690                 695                 700
Glu Lys Val Thr His Glu Glu Glu Lys Val Thr His Glu Glu
705                 710                 715                 720
Glu Lys Val Thr His Glu Glu Glu Asn Val Thr Tyr Glu Glu
                725                 730                 735
Glu Glu Lys Val Thr His Glu Glu Glu Glu Lys Val Met Lys Lys
                740                 745                 750
Lys Lys Ile Met Lys Tyr Lys Lys Lys Lys Lys Lys Lys Lys Gly
        755                 760                 765
Gly Gly Pro Ser Asn Ser
        770

<210> SEQ ID NO 2
<211> LENGTH: 2395
<212> TYPE: DNA
<213> ORGANISM: Leucocytozoon caulleryi

<400> SEQUENCE: 2
attttacatt ctacaact

```
aagaagaaaa agtaatacat gaagaagaaa aagaagaagt aatacatgaa gaagaaaaag    1500
aagaagtaac acatgaagaa gaaaagaag aagtaacaca tgaagaagaa aaagaagaag    1560
taacacatga agaagaaaaa gaagaagtaa cacatgaaga agaaaagaa gaagtaacac    1620 atgaagaaga agaaaaagta acacatgaag aagaaaaga agaagtaaca catgaagaag    1680 aaaagaaga agtaacacat gaagaagaag aaaagtaac acatgaagaa gaagaaaaag    1740
taacacatga agaagaagaa aaagtaacat atgaagaaga agaagaagaa gaagaaaaag    1800
taacacatga agaagaagaa aaagtaacac atgaagaaga agaaaaagta atacatgaag    1860
aagaagaaaa agaagaagat gaggaagaag aagaagaaga agaagaagaa gaggaagaag    1920
aagaagaaga agatgaggaa gaggaagaag aagaagaaga agatgaggaa gaggaagaag    1980
aagaagaaaa tgaggaagaa gaagaagaag aaaatgagga agaagaagaa gaagaagaag    2040
agcatgaaga agaagtaaca catgaagaag aagaagaaga aaaagtaaca catgaagaag    2100
aagaaaaagt aacacatgaa gaagaagaaa atgtaacata tgaagaagaa gaagaaaaag    2160
taacacatga agaagaagaa aaagtaacac atgaagaaga agaaaaagta acacatgaag    2220
aagaagaaaa tgtaacatat gaagaagaag aagaaaaagt aacacatgaa gaagaagaag    2280
aaaaagtaat gaagaagaag aagataatga agtataaaaa aaaaaaaaaa aaaaaaaaa    2340 aggggggggg gccatcgaat tcctaataga gctcgaattt ccccgatcgt tcaaa         2395

<210> SEQ ID NO 3
<211> LENGTH: 20
<212> TYPE: DNA
<213> ORGANISM: Artificial
<220> FEATURE:
<223> OTHER INFORMATION: An artificially synthesized primer sequence.

<400> SEQUENCE: 3
ggaaatgtgt ccttaacttc                                                20

<210> SEQ ID NO 4
<211> LENGTH: 21
<212> TYPE: DNA
<213> ORGANISM: Artificial
<220> FEATURE:
<223> OTHER INFORMATION: An artificially synthesized primer sequence.

<400> SEQUENCE: 4
cttcttcttc attactttt c                                               21
```